(12) United States Patent
L'Estrange et al.

(10) Patent No.: US 7,055,525 B2
(45) Date of Patent: Jun. 6, 2006

(54) RETENTION OF ORAL APPLIANCES FOR SLEEP RELATED DISORDERS

(76) Inventors: Peter L'Estrange, 36 Lee Park, London, SE3 9HZ (GB); Edward Pullen-Warner, 16 Lodge Avenue, Dartford, Kent DA1 3DX (GB); Victor Daltrey, 7 St. Margaret's Road, Ruislip, Middlesex HA4 7NX (GB)

( * ) Notice: Subject to any disclaimer, the term of this patent is extended or adjusted under 35 U.S.C. 154(b) by 265 days.

(21) Appl. No.: 10/168,691

(22) PCT Filed: Dec. 14, 2000

(86) PCT No.: PCT/GB00/04800

§ 371 (c)(1),
(2), (4) Date: Jun. 21, 2002

(87) PCT Pub. No.: WO01/45604

PCT Pub. Date: Jun. 28, 2001

(65) Prior Publication Data
US 2002/0189620 A1 Dec. 19, 2002

(30) Foreign Application Priority Data
Dec. 22, 1999 (GB) ................................ 9930445.3

(51) Int. Cl.
*A61F 5/56* (2006.01)
(52) U.S. Cl. ...................... 128/848; 128/859; 602/902
(58) Field of Classification Search ................ 128/846, 128/848, 859–862; 602/902; 433/6
See application file for complete search history.

(56) References Cited

U.S. PATENT DOCUMENTS

| 3,648,331 | A | * | 3/1972 | Kruger et al. | ............. | 24/113 R |
| 4,505,672 | A | * | 3/1985 | Kurz | ............... | 433/6 |
| 4,676,745 | A | * | 6/1987 | Zurita | ............. | 433/6 |
| 5,145,364 | A | * | 9/1992 | Martz et al. | .................... | 433/6 |
| 5,692,523 | A | * | 12/1997 | Croll et al. | ................. | 128/859 |
| 5,720,302 | A | | 2/1998 | Belfer | | |
| 5,947,724 | A | * | 9/1999 | Frantz et al. | .................. | 433/6 |
| 6,109,265 | A | * | 8/2000 | Frantz et al. | ............... | 128/862 |

FOREIGN PATENT DOCUMENTS

EP 0679378 2/1995

* cited by examiner

*Primary Examiner*—Michael A. Brown
(74) *Attorney, Agent, or Firm*—Dykema Gossett PLLC

(57) ABSTRACT

An oral appliance for the medical treatment of specific sleep related disorders, i.e., snoring and obstructive sleep apnoea, which has a number of sections for each jaw component which can be separated for ease of insertion and removal by patients. The separable components can be moved along an inherent guidance system and safely secured in the closed position by a bilateral locking mechanism. By virtue of the difference in paths of location of the main and the separate sections of each component, effective resistance to dislodgement of the appliance is obtained and maintained. This constitutes the claimed significant improvement in appliance retention.

16 Claims, 14 Drawing Sheets a b c a b a b c a b c a b c a b  c

RETENTION OF ORAL APPLIANCES FOR SLEEP RELATED DISORDERS

BACKGROUND OF THE INVENTION

1. Field of the Invention

THIS INVENTION relates to a means of providing a significant increase in the retention of oral appliances designed for the treatment of sleep related disorders, namely snoring and obstructive sleep apnoea (OSAX with consequent health benefits.

2. The Prior Art

Snoring and sleep apnoea are caused by partial or total collapse of the upper airway during sleep. Reduction in muscle tone at the beginning of sleep together with structural factors such as obesity, retro-positioning of the face, retrognathia, tonsillar hypertrophy and macroglossia have been proposed as aetiological factors. There is a wide spectrum of severity from the simple snorer to the patient with very severe sleep apnoea. All patients with obstructive sleep apnoea snore but not all snorers have sleep apnoea. A large proportion of subjects fall into the middle of this spectrum with variable amounts of snoring and OSA.

The creation of a pneumatic stent for the upper airway by means of a facial mask and a calculated pressure of air is a safe and effective method of treatment for both snoring and OSA. This approach to treatment is referred to as nasal continuous positive airway pressure (CPAP) and has for many years been the gold standard for treatment of these conditions. For patients who are simple snorers or those who have OSA with or without excessive daytime sleepiness, CPAP may be an unacceptable method of treatment and other alternatives need to be evaluated. Although compliance with CPAP is generally considered to be high, there is increasing evidence of a lower level of compliance than previously considered with consequent health risk. A surgical approach to the soft palate can be employed for those patients who are simple snorers or who have mild OSA, but this is not considered a safe and effective method of treatment for those patients with moderate or severe OSA, and moreover the long term effectiveness of such procedures has yet to be evaluated.

More recently, oral appliances have been proposed as an alternative to CPAP. Many of these devices depend for their effectiveness on being able to satisfactorily hold the lower jaw and tongue in a forward position during sleep in order to enlarge the airway behind the tongue, and this group of appliances are known as mandibular advancement splints (MAS). In order for the tongue to be able to stay forward, it is important for the tension on the major muscle of the tongue (the genioglossus) and the pharyngeal muscles to be maintained.

Limitations in Terms of Retention of Present Oral Appliances

Visual endoscopic examination during simulated sleep (sleep nasendoscopy) with the wearing of appliances which are designed to hold the tongue and jaw in a forward position shows that if a close relationship of the appliance to the natural teeth is not maintained, even if the displacement occurs to a small degree, the tongue and soft palate drop back in the throat narrowing the airway, and as a consequence this reduces the effectiveness of the appliance. These observations undoubtedly contribute to the results reported in randomized cross-over studies of oral appliances and CPAP where the same level of effectiveness as CPAP is not generally achieved with the oral appliance. The effectiveness of treatment is evaluated in terms of reduction of the so-called respiratory dysfunction index (RCI or AHI-Apnoea hypopnoea index), calculated by comprehensive, complex overnight sleep studies (polysomnography). In addition, the oral appliances as a general rule do not fully maintain the desired hight levels of oxygen saturation in the blood essential to the maintenance of full body function including the brain. For these reasons it has been considered that oral appliances which advance the lower jaw may only be considered an effective method of treatment in some patients with simple snoring and mild and moderate OSA.

All oral appliances used with patients who have their own natural teeth therefore depend for their effectiveness on maintaining that vital apposition with the teeth during sleep. This is achieved by engaging surfaces of the teeth which are below their line of greatest contour to a lesser or greater degree in order to provide resistance to displacement, the so-called "retention" of the appliance. Where the material used for construction of the appliance is of an all enveloping soft resilient material (e.g., polyvinylacetate-polyethylene polymer) or a combination of a harder outer casing with a soft resilient inner lining (poly carbo lactone), the outer surface of the teeth can usually be engaged for retentive purposes. Because the softer material on the inner aspect has the capacity to deform during insertion and removal of the appliance, it can also deform and be displaced during sleep if the pull of the lower jaw during sleep is considerable. If the material used for construction of the appliance is of a relatively harder unyielding nature, e.g., polymethyl methacrylate or metal, it is better capable of holding the lower jaw in a forward position and offering resistance to the forces to which it may be subjected with minimal distortion when compared with a flexible material. With appliances constructed of a metallic cast material, extensions of the base material in the form of dental clasps into the areas below the line of greatest contour afford retention. Where other more rigid non-metallic materials are employed, the material may be extended into the undercut regions in a thinner section so that a degree of flexion in these zones is possible or wrought stainless steel wire extensions are used to form dental clasps for retention. The limitation in terms of the degree of retention which can be obtained with this approach is that only a small proportion of the undercut area available for retention can be usefully engaged (e.g., approximately 10%) due to the essential requirement for the patient to be able not only to insert the appliance without undue difficulty but equally importantly to be able to remove it. The clinical assessment of how much retention has been achieved by this approach to gaining retention is made on a purely arbitrary basis while the patient is conscious. It bears little relationship to the retention and stability during sleep when very large displacing forces can come into effect, not only in terms of attempted jaw opening but also in relation to extreme lateral jaw excursions. As the degree of severity of OSA increases the retention of the appliance becomes more critical which probably accounts for the lack of published success of oral appliances generally for severe OSA on an equally effective basis when compared with CPAP.

Another disadvantage of conventional methods of providing retention with current oral appliances (based on a unidirectional path of insertion and removal) is that untoward forces can be exerted on the surface of existing crowns, bridges and other dental restorations during insertion, removal and displacement during sleep which can result in their loss from the teeth or damage with much discomfort to patient and dentist alike. From these observations it can be concluded that that the ideal method of gaining retention for an appliance for sleep related disorders would include a method of insertion and removal which permits a passive relationship with the supporting teeth, ease of insertion and removal yet at the same time maintains that necessary vital apposition to the teeth in order to resist displacing forces during sleep.

SUMMARY OF THE INVENTION

The present invention addresses these requirements and it provides and intra-oral device for treatment of sleep:related disorders comprising a main body for engagement in a first direction with teeth of one jaw of the user, a secondary body for engagement in a second direction with said teeth of the same jaw, and detent means for releasably retaining the main body and secondary body in clamped engagement with the interposed teeth. Further, the necessary retention is achieved by total engagement of all undercuts available on the infra-bulge aspects of the buccal (cheek) surfaces of the posterior teeth of both jaws (i.e., 100%), whether these undercut regions are naturally occurring or artificially created by existing dental procedures to ensure that retention can be effectively provided. For these aims to be achieved with a rigid material, the components which relates to each jaw has to consist of more than one part using a multidirectional path of insertion and removal.

The aim of the present invention is to provide an alternative means of achieving retention for oral appliances used in the treatment of snoring and obstructive sleep apnoea with the specific purpose of resisting displacing forces during sleep in such a manner that they will be more effective than those currently available. The structural features which differentiate our device from those currently available relate to the means of gaining the retention by using at least two, and preferably three, rather than a single component for the elements which attach to the lower and upper jaws respectively. The concept of using a multi-rather than a unidirectional path of insertion produces an appliance which has the capacity to effectively resist displacement, limit potential damage to dental restorations (i.e., crowns, bridges and veneers) by allowing the primary components of the device to be formed from a relatively rigid material without compromising the engagement of the inner surface of that device with the buccal undercut surfaces of the teeth. At the same time the patient can activate and release the device by manual activation of a locking mechanism. Whilst the locking mechanism is in place, the device cannot be removed. The superior retention is obtained by engaging undercuts on the buccal (outer-cheek) surfaces of the teeth whether these be naturally occurring or artificially created. The use of laterally guided sections which constitute the second and third parts of the component for both upper and lower jaws enables engagement of these buccal and interstitial (the areas between the teeth on the cheek side) surfaces. The first part of the upper and lower jaw components covers the occlusal (biting) surface and lingual/palatal (tongue side) surfaces.

The engagement of the lateral aspects of the natural teeth is achieved either by rotation of the lateral extensions or by means of a horizontal guidance system, the selection of which is dictated by the morphology of the natural teeth. A spring locking or camming mechanism may be provided for either of these approaches which is simple to operate by the patient but when activitated will ensure that both upper and lower jaw components are securely retained in place against the natural teeth during sleep.

The relatively rigid material of choice for current oral appliances used for the treatment of snoring and sleep apnoea is polymethyl methacrylate denture base material with or without the incorporation of stainless steel retentive dental clasps. Metal castings have been use to give greater strength and rigidity but reference to the use of metals for these oral appliances is scant. We have used castings of cobalt chromium alloys to construct rigid appliances for the medical conditions referred to, using standard cast dental clasps for the purpose of gaining retention. The stronger and the more rigid the material selected, the greater the likelihood of the appliance being more effective in maintaining the tongue in a forward position. A disadvantage of metallic splints is that they are more time consuming to fabricate than polymethyl methacrylate materials and do not lend themselves readily to any subsequent modifications in terms of alterations in tooth contour produced by routine dental care. From a functional point of view and with patients with very strong jaws, they are superior to other materials. Other materials such as polycarbonates are also available but as with metallic castings, the techniques required for their fabrication are more complex.

For the invention described in this application, each of the upper and lower jaw components can be constructed from relatively rigid materials such as cast gold or cobalt chromium dental casting alloys or polymethyl methacrylate denture base materials. Where the first part is constructed of a cast dental alloy, the second and third parts will incorporate an autopolymerising methyl methacrylate material as a support framework for other components. The guiding mechanism for the second and third parts together with the spring locking or camming mechanism will be constructed from dental stainless steel wire and tubing irrespective of whether the appliance is constructed of a polymethyl methacrylate material or a cast dental alloy. Each upper and lower jaw component will consist of three sections namely the main body (referred as the first part) and two lateral extensions (referred to as the second and third parts).

When these extensions are united with the main body of the jaw component by means of the guidance and spring locking or camming mechanisms, the upper and lower jaw components will have the appearance of being of unit construction. Bearing in mind that the various designs of construction of oral appliances for the medical conditions to which reference has been made may be rigidly joined or alternatively in an articulated manner, the method of gaining retention for each jaw component outlined in this application remains the same, i.e., the principle of gaining the retention is universal and is independent of individual appliance design. The selection of cobalt chromium alloys as the material of choice will be dictated by the functional demands likely to be made on the appliance by the individual patient, a condition likely to be more prevalent in the severe sleep apnoea patient. Metallic castings are also more likely to securely contain all components—it is unlikely that they would ever be inadvertently fractured or distorted, an important safety aspect of design.

Claim is made to all principles, designs and variations thereof where oral appliances for the treatment of snoring and OSA comprising of more than one separate part for use on or about upper and/or lower jaws either singularly or in combination where the union and fixation thereof is obtained by uniting those parts or combinations thereof is used to obtain non-displacement of the appliance by means of rods or tubes, slots and rails and variations thereof (trombone principle), screw action closures, the use of springs (both tension and compression), bolts and variations thereof, magnets, hooks, cleats and tags and any device used to unite and hold close together appliances and devices for the purpose of anchorage and non displacement of all or parts of such appliances and devices to ensure maximum efficiency of any oral appliance for snoring and OSA or part thereof.

Specific embodiments of the invention are described by way of example only with reference to the accompanying drawings in which:

BRIEF DESCRIPTION OF THE DRAWINGS

FIG. 5(b) illustrates the tag (7) attached to the bearing sleeves for retention within the enveloping acrylic resin.

FIG. 9(a) shows the appliance in the closed position and FIG. 9(c) in the open position. FIG. 9 (8) indicates the guide and support davit employed to provide the sliding rotational path of engagement. The arrows shown in FIG. 9(c) indicate the range of movement possible with this system of engagement. A cross-sectional view is shown through the posterior teeth in FIG. 9(b), illustrating characteristic undercut regions of the posterior teeth, buccal (cheek) to the left, lingual (tongue) to the right of the diagram.

FIG. 14 (c,d) shows side views of the cam operating mechanism in the closed (c) and open (d) positions.

DETAILED DESCRIPTION OF THE PREFERRED EMBODIMENT

The invention is essentially the means of providing retention as described (or any modification thereof) which can be incorporated into any oral appliance to be employed for the treatment of patients with snoring and/or obstructive sleep apnoea.

The structural features of our invention in terms of gaining retention for an oral appliance differentiate it from other oral devices currently employed for the treatment of snoring and/or sleep apnoea. The ability to rigidly engage the undercuts (either naturally occurring or artificially created) on the buccal aspects of the posterior teeth by rigid extensions of the appliance is unique to our method of design and construction. Whether the oral appliance has solidly joined upper and lower components (as in a conventional sports gumshield) or those that are separate for each jaw with a variety of types of connectors which permit relative movement between the two components, the method of gaining retention for the appliance using our invention can be employed. Although the lateral sections (independent of the guidance system for insertion) are conjoint with the main body of each jaw component, they are capable of elective displacement for the purpose of insertion and removal.

Figure 1:
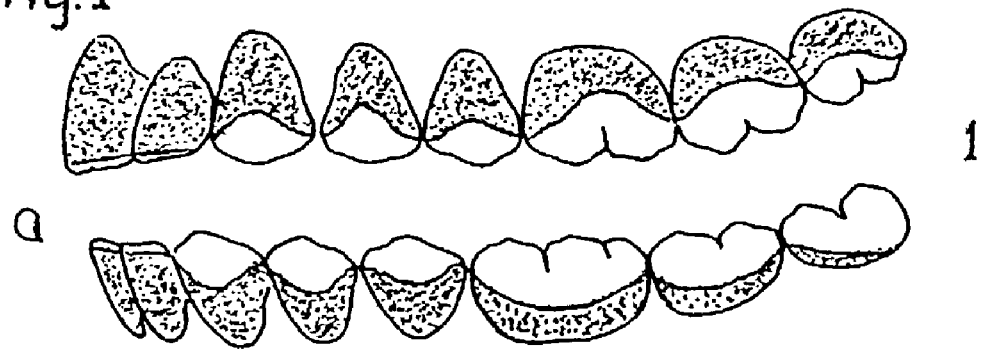
FIG. 1 illustrates lateral (a,c) and cross-sectional (b) views of the lines of contour (1) revealed by surveying the posterior natural teeth. The stippled areas indicate the areas below the line of contour (survey line) which can be utilized for gaining retention of the appliance (referred to as undercut regions).
Figure 1:
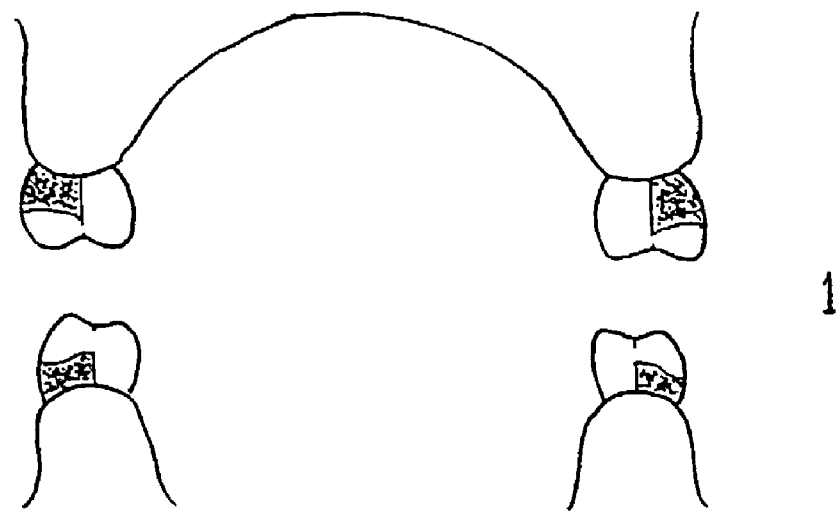
Figure 1:
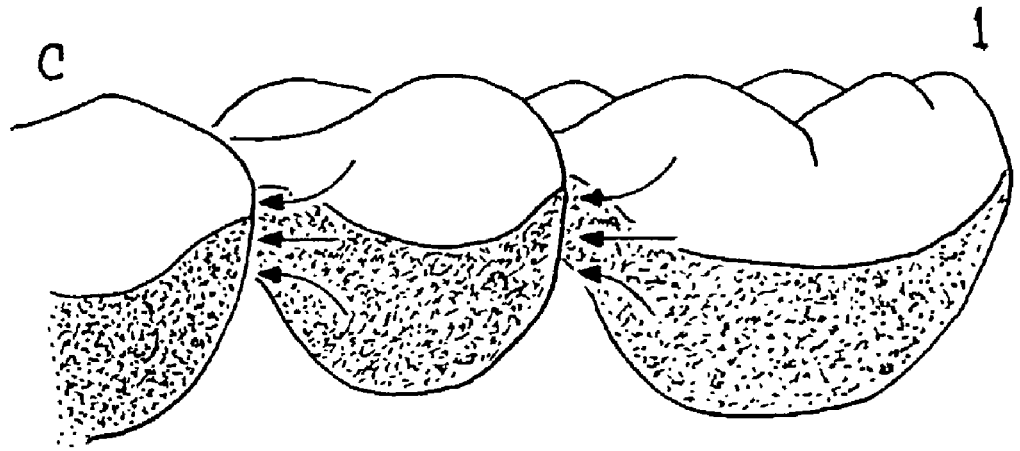
Figure 2:
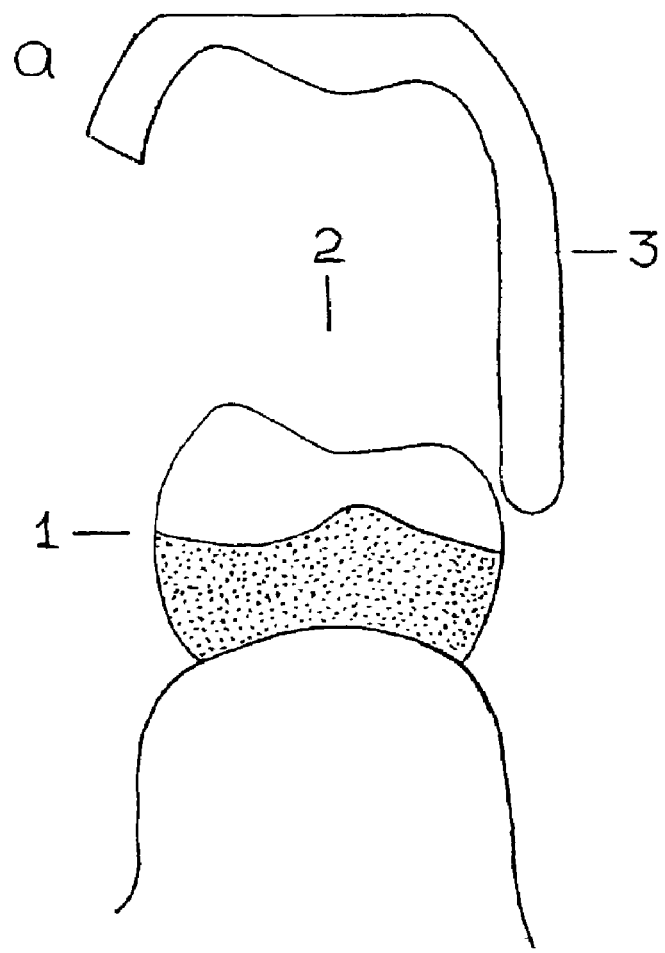
FIG. 2 is a cross-sectional view through the posterior dental arch showing the path of insertion (2) of the main body (3) of a jaw component and its relationship to the line of contour (1) and undercut regions prior (a) and subsequent (b) to its insertion by the patient—tongue side to the right and cheek side to the left of the figure.
Figure 2:
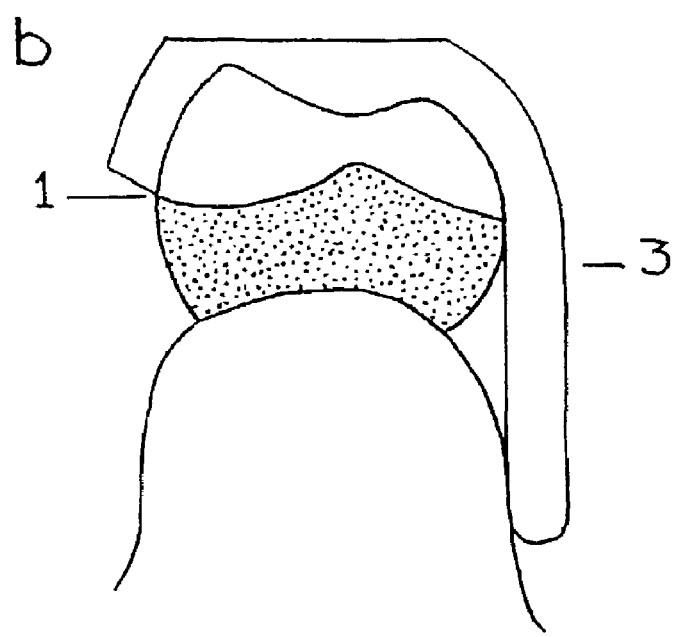

The first embodiment of our device relates to the main body of each jaw component of oral devices used in the treatment of snoring and/or obstructive sleep apnoea. FIGS. 1 and 2 illustrate this component (3) and its path of insertion (2) in relation to the undercut regions (1) of the posterior natural teeth. The direction of this path of insertion is substantially parallel to the long axis of the teeth and abuts the linqual or palatal surfaces of the teeth. In order that this component shall remain passive in relation to the teeth, any undercut zones not compatible with the chosen path of insertion will be eliminated during the construction of the main body in order to avoid pressure on the natural teeth during insertion and removal (FIG. 2). The main body of the device can be manufactured of polymethyl methacrylate or cobalt chromium alloy in order to afford rigidity to the construction. It has a generally L-shaped cross section.

Figure 3:
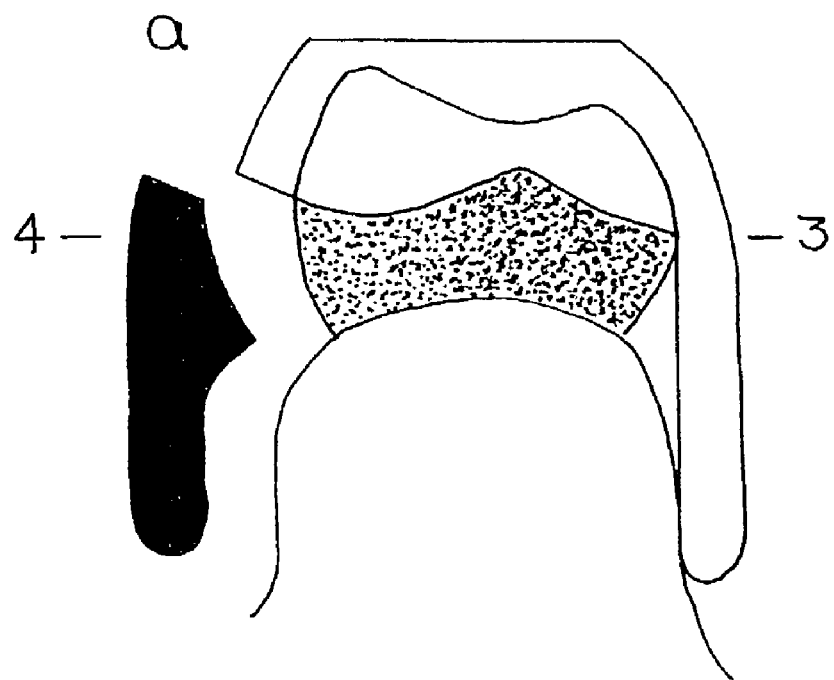
FIG. 3 illustrates in a cross-sectional view the relationship of the lateral sections (4), (a) prior and (b) subsequent to their engaging the undercut regions on the buccal (cheek) side of the posterior teeth.
Figure 3:
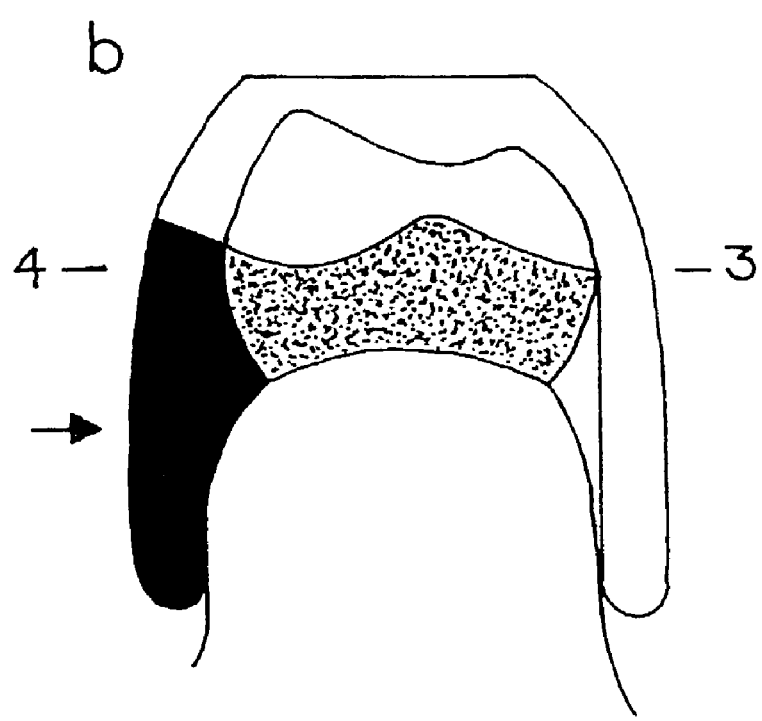
Figure 4:
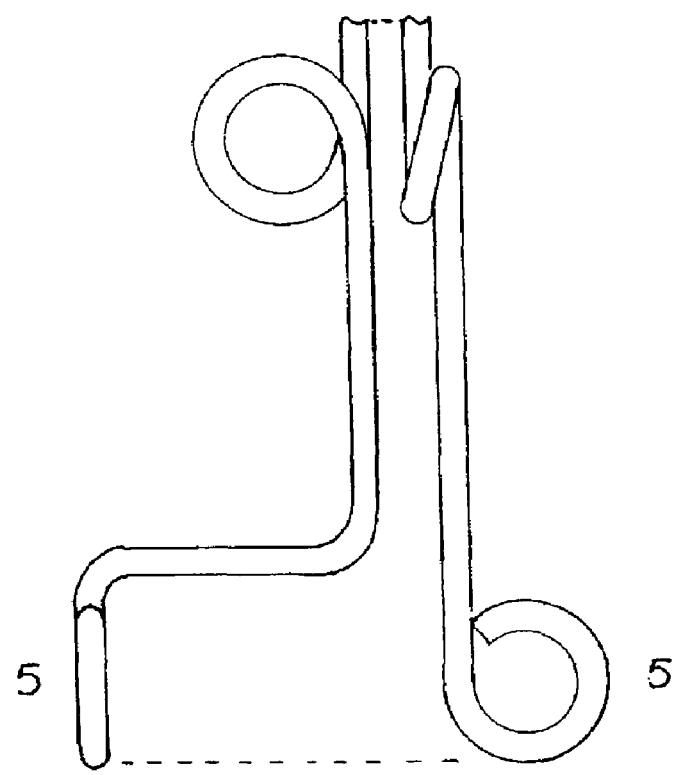
FIG. 4 illustrates the design of the spring lock (5) associated with a horizontal guidance system for the lateral sections.
Figure 5:
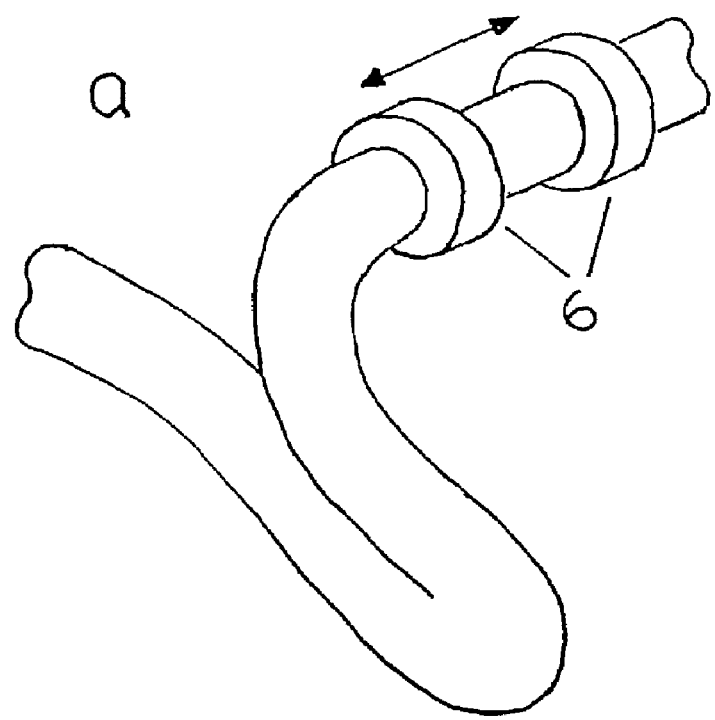
FIG. 5 represents lateral perspective (a) and cross-sectional (b) views of the bearing sleeves (6) which form a part of the horizontal guidance system together with an indication of the range of movement of the sleeve between open and closed positions (see arrows).
Figure 5:
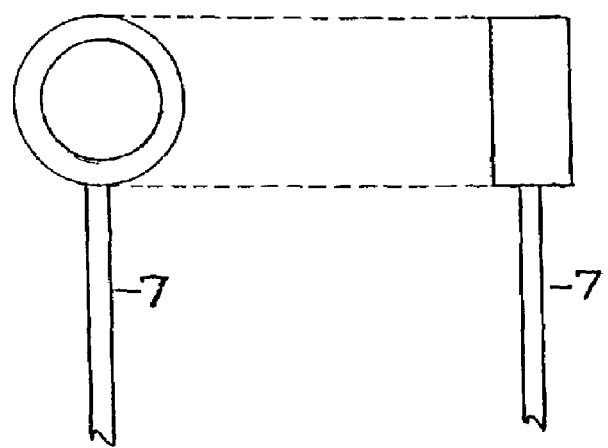
Figure 6:
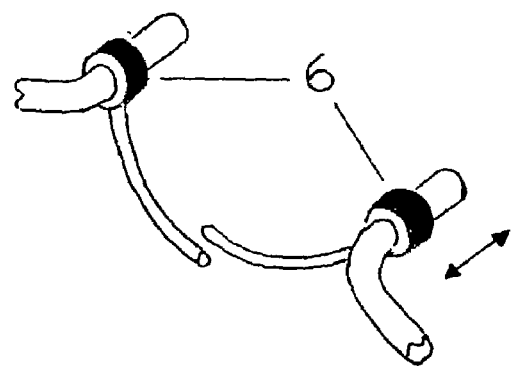
FIG. 6 is a lateral perspective (a) and cross-sectional views (b,c) of the bearing sleeves (6) which form a part of the horizontal guidance system and are incorporated within the lateral sections by retentive tags (7) (FIG. 5, (b)). The cross-sectional views illustrate the spring locking mechanism (5) in both open (b) and closed (c) positions.
Figure 6:
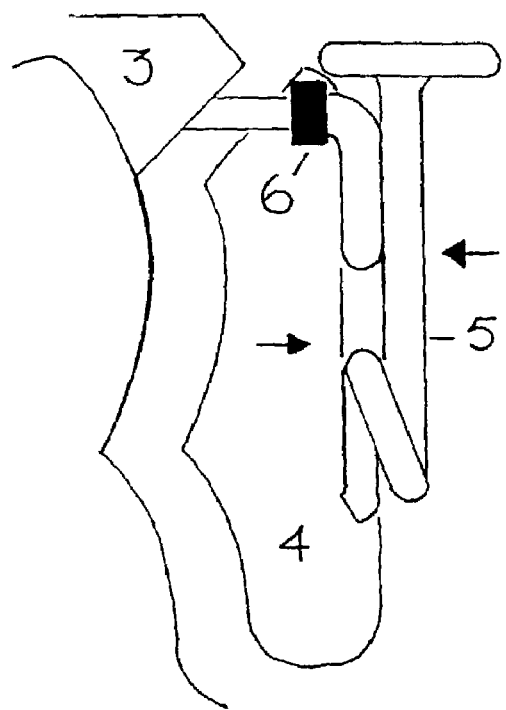
Figure 6:
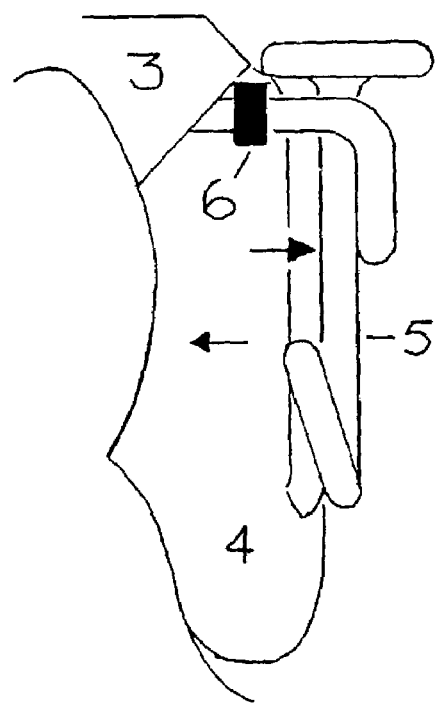
Figure 7:
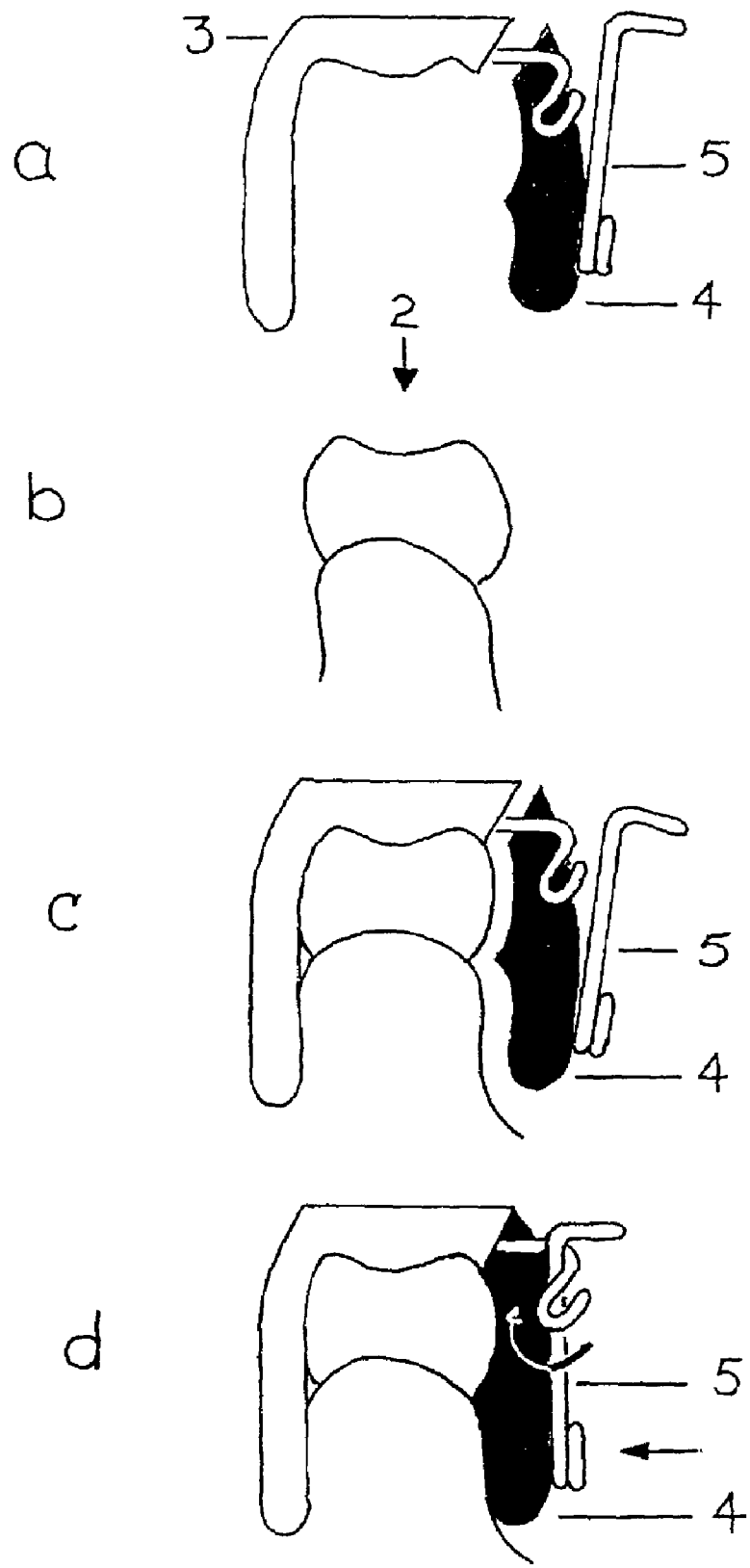
FIG. 7 is a cross-sectional view of the posterior teeth showing the relative paths of insertion of the main component (3),(a,b c) and lateral sections (4), (a,d) and the spring locking mechanism (5). This is for an appliance using a horizontal guidance system for the location of the lateral rigid extensions (4) of the upper and lower jaw components.
Figure 8:
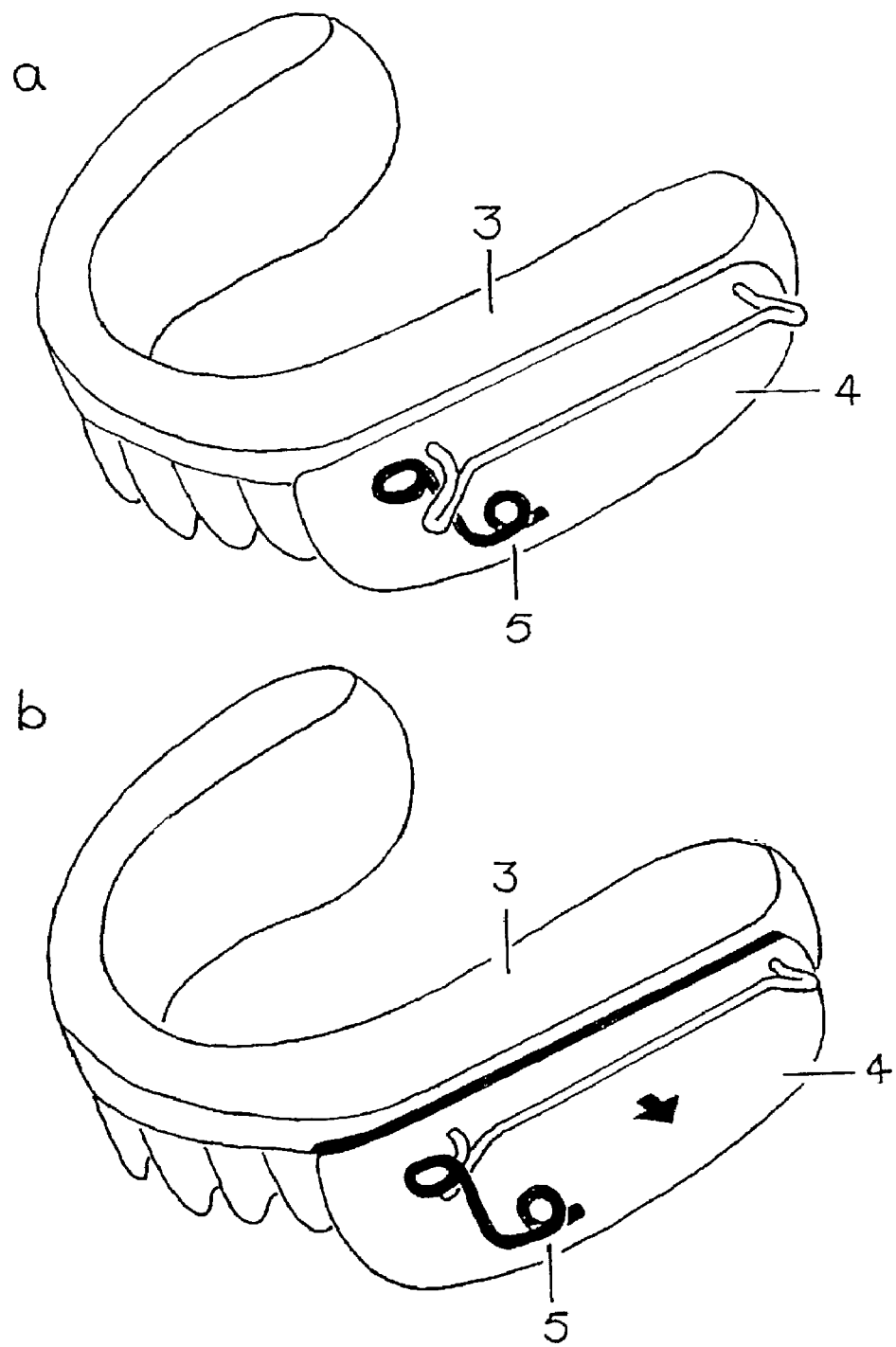
FIG. 8 is a lateral perspective view of the lower jaw showing the main component (3) and lateral sections (4) in the closed (a) and open (b) positions together with the spring locking system (5) used for components where the lateral sections have a horizontally guided path of insertion and withdrawal.
Figure 9:
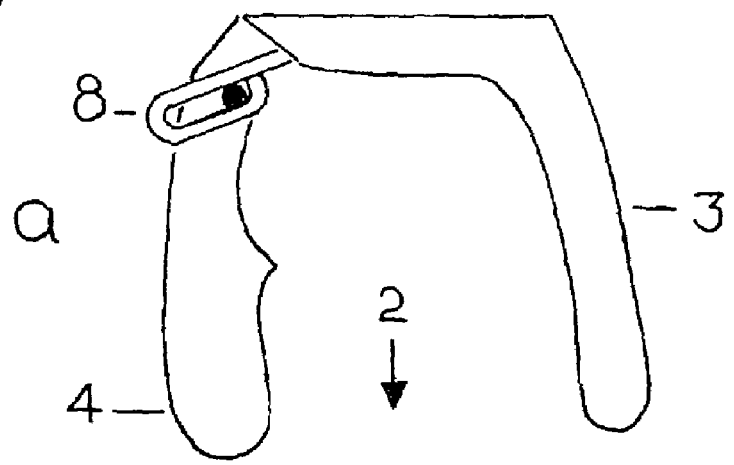
FIG. 9 illustrates the principle of gaining rigid buccal retention for each jaw component by means of a sliding rotational path (as an alternative to a horizontal guidance system) for engagement of the buccal undercuts (1) of the posterior teeth by the lateral sections (4).
Figure 9:
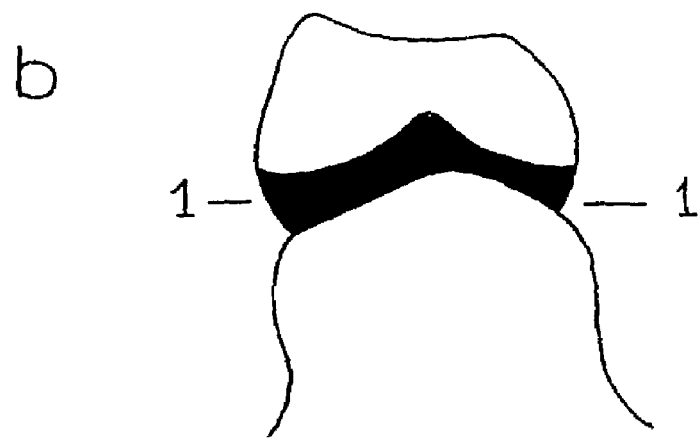
Figure 9:
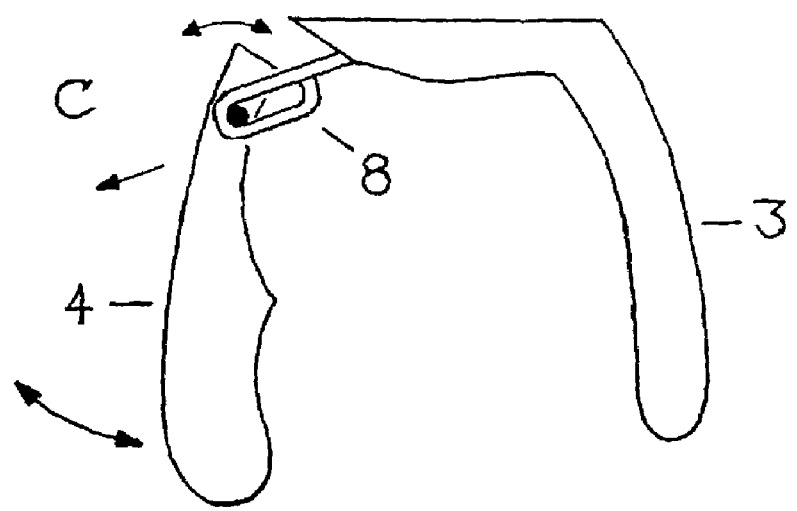
Figure 10:
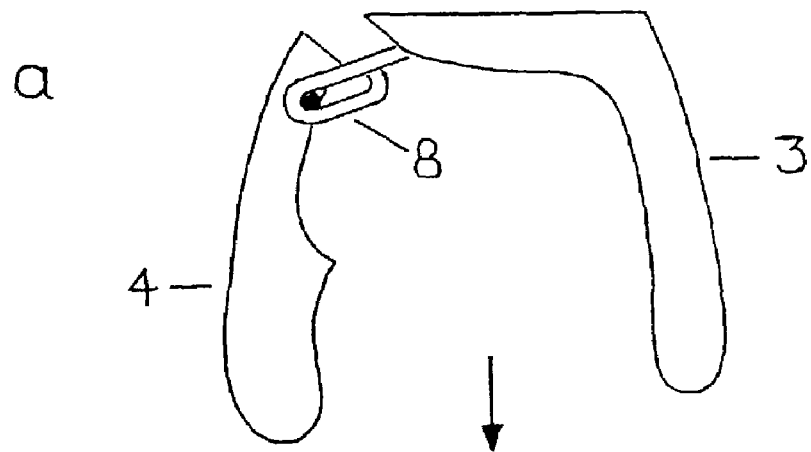
FIG. 10 demonstrates the sequence of insertion and in reverse order, of removal, of the jaw component where a sliding rotational method is employed for engagement of the buccal (cheek) undercut surfaces of the posterior natural teeth (a,b,c).
Figure 10:
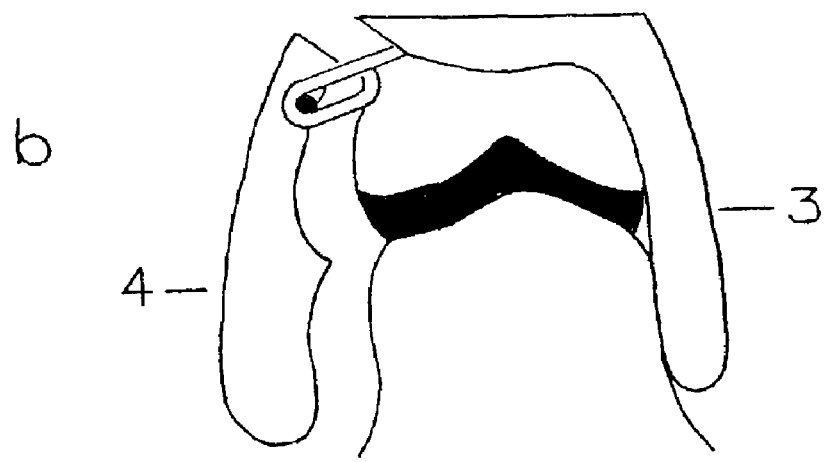
Figure 10:
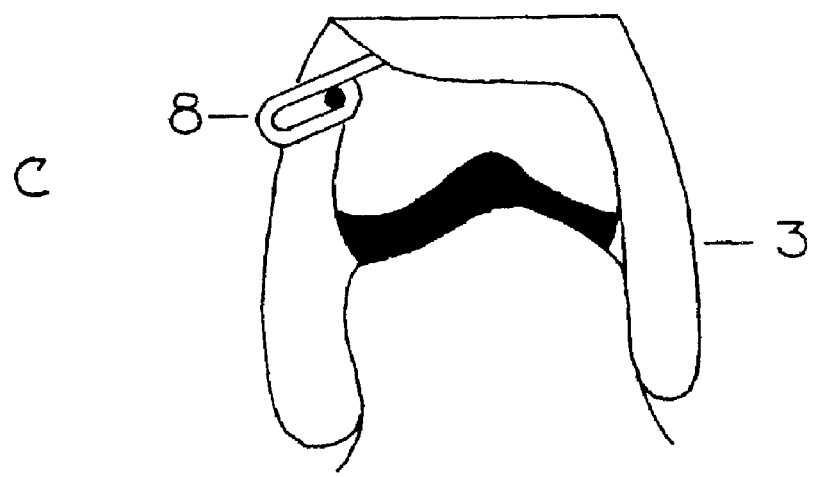
Figure 11:
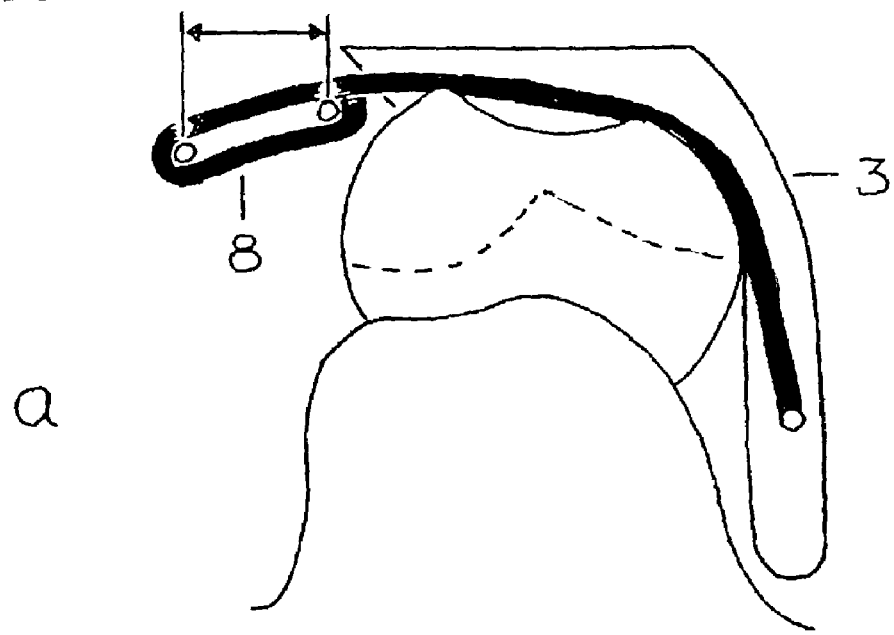
FIG. 11(a) shows the design of the guide and support davit (8) for sliding rotational sections. The range of lateral displacement is indicated by arrows. The action of the locking system in both closed (b) and open (c) positions is illustrated.
Figure 11:
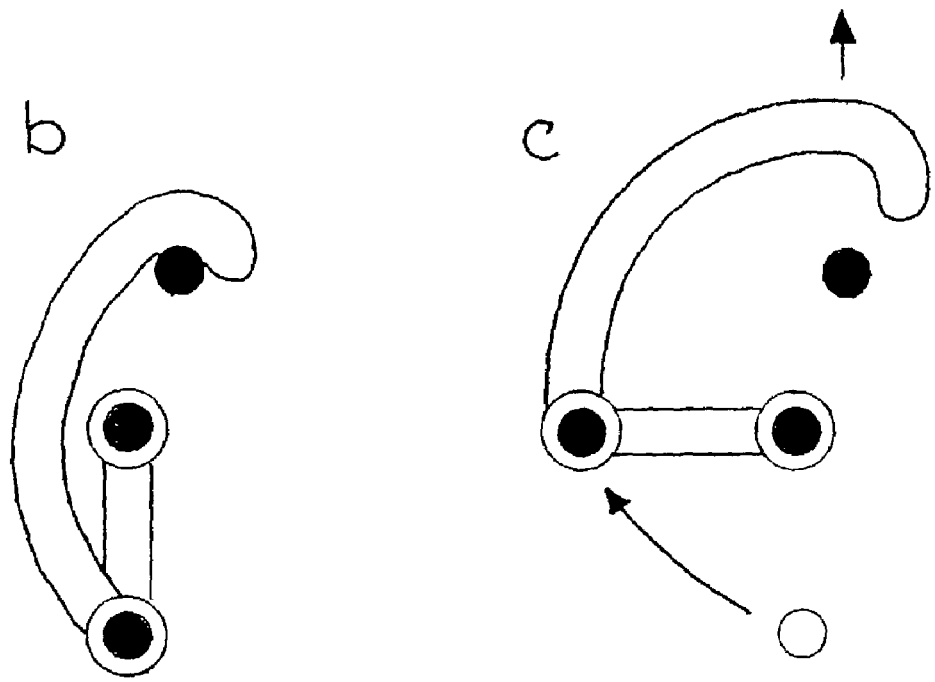

The second embodiment relates to a secondary body or lateral section (4) which permits engagement with the teeth in a direction substantially orthogonal to the direction of the main body. The third embodiment relates to the guidance system which enables passive engagement of the lateral aspects of the teeth. This system may be horizontally guided as illustrated in FIGS. 3,7 and 8 or sliding rotational as depicted in FIGS. 9, 10, 11, 12, 13 and 14. In relation to the horizontal guidance system, the extent of lateral movement necessary in order to release these lateral sections from the natural teeth is illustrated in FIGS. 3,7 and 8. Bearing sleeves (6) mounted on support members are provided to ensure a smooth movement of the lateral sections during insertion and removal and these are to be seen in FIGS. 5 and 6. These bearing sleeves consist of stainless steel tubing and engage stainless steel wire support members (if the main body of the jaw component is constructed of polymethyl methacrylate) or cobalt chromium support members (if the main body is constructed of cobalt chromium alloy). The secondary body or lateral section will be constructed in auto-polymerising acrylic resin and will incorporate the various supplementary components for both alternative types of material selected for the construction of the main body.

Where a sliding rotational system for engagement of the secondary body or lateral section is clinically indicated, a guide and support davit is incorporated (8) and its design, range and direction of control is depicted in FIGS. 9,10,11, 12, 13 and 14.

Figure 12:
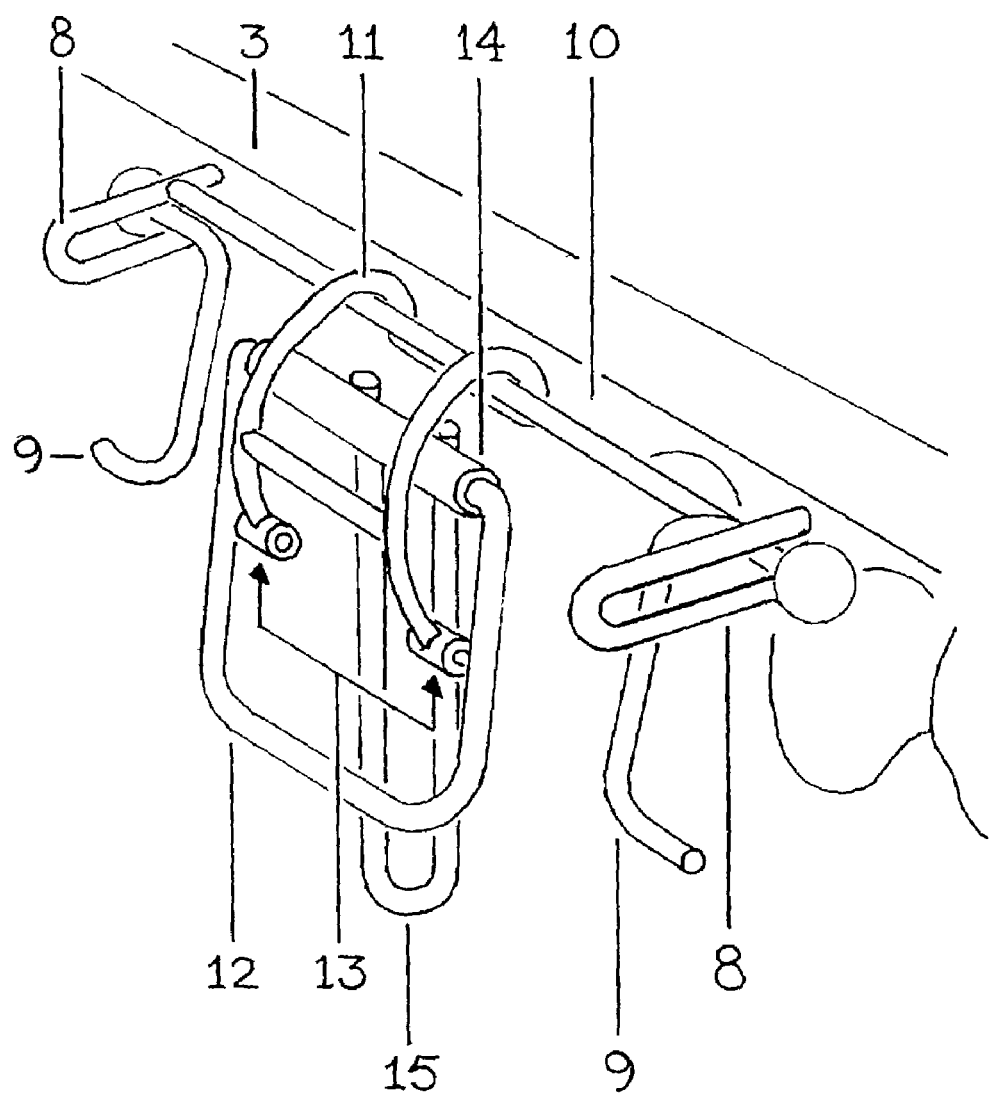
FIG. 12 shows a complete overall view of the components for sliding rotational lateral sections.
Figure 13:
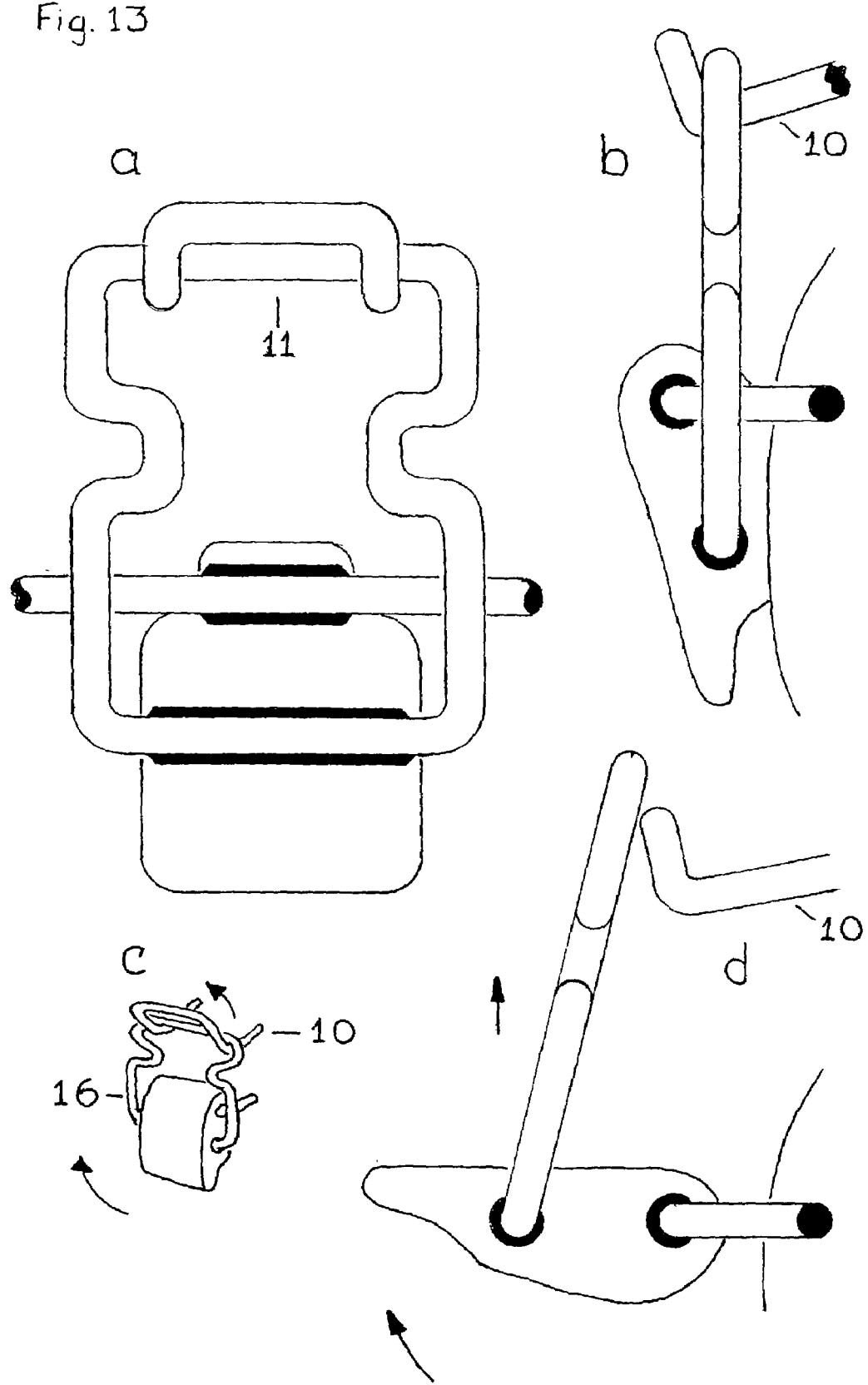
FIG. 13 (a,b,c,d) shows an alternative latch design (16). The principle remains the same as that shown in FIG. 12. The essential difference is that the brace bar (10) is independent of the davits (8) and emanates from the main body (3) of the appliance.
Figure 14:
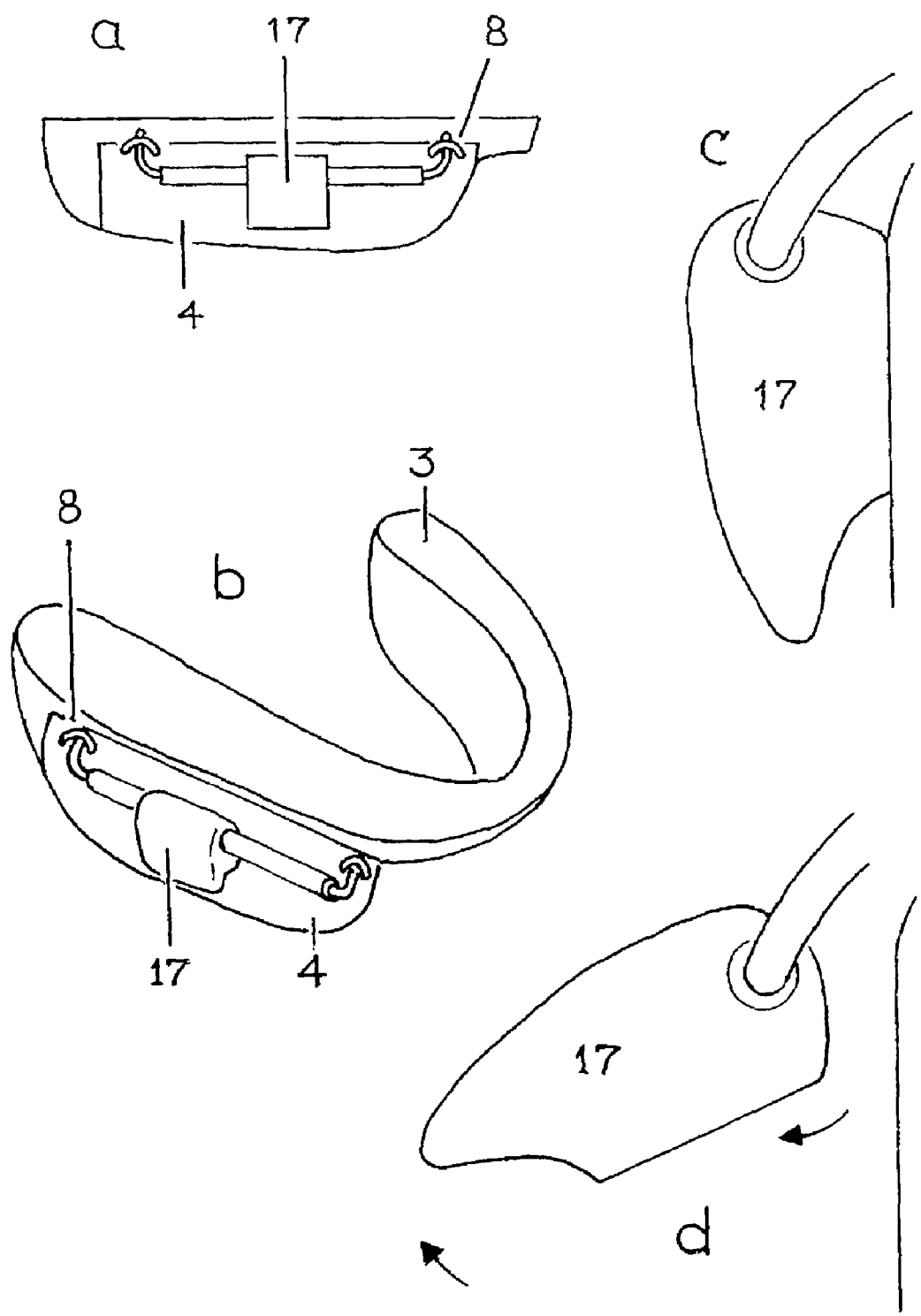
FIG. 14 (a,b,c,d) shows an appliance with rotating lateral sections where the locking mechanism consists of a rotating cam (17) which applies positive pressure to hold the lateral sections in place against the buccal tooth surfaces of the posterior teeth thereby preventing any possibility of displacement.

The fourth embodiment relates to the method of union of the secondary body (4) to the main body of the jaw component (3). This comprises a first element and a second element releasably securable by respective detent means to the main body. Where the guidance system for the engagement of the lateral aspects of the teeth is of the horizontal type, the detent means comprises a resiliently deformable arm mounted on one of the bodies, and movable between a first position in which the bodies are free to move independently and a second position in which the arm engages a hook on the other body to secure the bodies in engagement with the interposed teeth. This spring lock mechanism is illustrated in FIGS. 4,6,7 and 8. Stainless steel wire is used for its fabrication and it holds the secondary body (4) in close apposition with the main body (3) of each jaw component under spring tension (FIGS. 6,7, and 8), thereby preventing inadvertent separation of the main and secondary bodies during sleep. The means of locking and unlocking of the detent means is activated manually by the patient.

Where a sliding rotational system is selected for construction, the respective detent means consists of a latch or cam mechanism and its application is shown in terms of the detailed stainless steel wire components in FIGS. 12, 13 and 14. Both the latch and cam mechanism use the principle of spring tension to apply positive pressure between two interfaces. That is to say, a buccal flange surface engaging a compatible surface on the palatal or lower lingual component of the appliance. In FIG. 12, these components comprise a support and guiding davit (8), guide pins (9), brace bar (10), latch claw (11), latch handle (12), claw pivot (13), latch pivot (14) and latch pivot retention loop (15). FIG. 13 (a,b,c) show side views of the alternative latch (16) in the closed position. FIG. 13 (c) illustrates the latch in the open position. Arrows shown in FIG. 13 (c, d) indicate direction of movement during opening. Latch closure is in the reverse direction. FIG. 14 (a,b) shows lateral and oblique views of the lower component of the appliance with the cam (17) in the closed (locked) position. FIG. 14 (c) shows a side view of the cam (17) in the closed (locked) position and FIG. 14 (d) illustrates a side view of the cam (17) in the open (unlocked) position.

Where a cobalt chromium alloy is selected for construction of the main body, the components which are integral with that body would be cast in cobalt chromium alloy.

It should be appreciated that various other changes and modifications may be made to the embodiments described without departing from the scope of the invention defined in the following claims.

The invention claimed is:

1. An oral device for treatment of sleep-related disorders comprising a main body for engagement in a first direction with teeth of one jaw of the user, a secondary body for engagement in a second direction with said teeth of the same jaw, and detent means for releasably retaining the main body and secondary body in clamped engagement with said teeth, wherein the oral device includes guide means for controlling translation of the secondary body during engagement with the teeth, said guide means comprising support members projecting laterally from the main body, and wherein the secondary body comprises bearing sleeves mounted on the support members to guide the translation of the secondary body relative to the main body.

2. An oral device according to claim 1, wherein the secondary body abuts more than 20% of the buccal undercut surfaces of said teeth.

3. An oral device according to claim 1, wherein the main body is moved into engagement with said teeth in a direction substantially parallel to longitudinal axes thereof.

4. An oral device according to claim 1, wherein the secondary body is moved into engagement with said teeth in a direction substantially orthogonal to the direction of engagement of the main body.

5. An oral device according to claim 1, wherein the secondary body comprises a first element and a second element releasably securable by respective detent means to the main body.

6. An oral device according to claim 1, wherein the main body abuts occlusal and lingual surfaces of the teeth.

7. An oral device in claim 1, wherein the detent means are manually actuable.

8. An oral apparatus for treatment of sleep-related disorders comprising first and a second oral devices,
    said first oral device for engaging a first set of teeth of a first jaw of a user and comprising a main body for engagement in a first direction with said first set of teeth, a separate secondary body for engagement in a second direction with said first set of teeth, and detent means for releasably retaining the main body and secondary body in clamped engagement with said first set of teeth, and
    said second oral device for engaging a second set of teeth of a second jaw of said user and comprising a main body for engagement in a first direction with said second set of teeth of said second jaw of the user, a separate secondary body for engagement in a second direction with said second set of teeth, and detent means for releasably retaining the main body and secondary body in clamped engagement with said second set of teeth, wherein said main and secondary bodies of said first and second oral devices are made of rigid material.

9. An oral apparatus according to claim 8, wherein the detent means comprises a resiliently deformable arm mounted on one of the bodies and movable between a first position in which the bodies are free to move independently and a second position in which the arm engages a hook on the other body to secure the bodies in engagement with said teeth.

10. An oral apparatus according to claim 8, wherein the detent means comprises a camming member pivotally mounted with respect to the second body.

11. An oral device as claimed in claim 8, including means for pivotally connecting the first and second oral devices.

12. An oral apparatus according to claim 8, wherein said main bodies and said secondary bodies are made of a rigid material selected from the group consisting of metals, polymethylmethacrylate and polycarbonates.

13. An oral apparatus according to claim 8, bodies have generally L-shaped cross-sections.

14. An oral apparatus according to claim 8, wherein each of said detent means comprises bearing sleeves and cooperating spring lock elements.

15. An oral apparatus according to claim 8, wherein each of said detent means comprises guiding davits and cooperating guide pins.

16. An oral apparatus as claimed in claim 8, including means to rigidly connect said first and second oral devices together.

* * * * *